(12) United States Patent
Yaku et al.

(10) Patent No.: US 7,320,866 B2
(45) Date of Patent: Jan. 22, 2008

(54) DISCRIMINATION METHOD OF TARGET BASE IN DNA, AND ALLELE SPECIFIC PRIMER USED IN THE METHOD OF THE SAME

(75) Inventors: Hidenobu Yaku, Osaka (JP); Hiroaki Oka, Osaka (JP); Tetsuo Yukimasa, Kanagawa (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 11/607,900

(22) Filed: Dec. 4, 2006

(65) Prior Publication Data

US 2007/0281340 A1 Dec. 6, 2007

(30) Foreign Application Priority Data

Jun. 5, 2006 (JP) .............................. 2006-156324

(51) Int. Cl.
*C12Q 1/68* (2006.01)
*C12P 19/34* (2006.01)

(52) U.S. Cl. ......................................... 435/6; 435/91.1

(58) Field of Classification Search ..................... None
See application file for complete search history.

(56) References Cited

U.S. PATENT DOCUMENTS

| 6,750,018 B2 | 6/2004 | Kambara et al. |
| 6,794,133 B1 | 9/2004 | Ausubel et al. |
| 2003/0049628 A1 | 3/2003 | Kambara et al. |
| 2003/0148301 A1 | 8/2003 | Aono et al. |
| 2003/0186314 A1 | 10/2003 | Kambara et al. |
| 2004/0197803 A1* | 10/2004 | Yaku et al. ............ 435/6 |

FOREIGN PATENT DOCUMENTS

| JP | 2002-101899 | 4/2002 |
| JP | 2004-248635 | 9/2004 |
| JP | 2005-065688 | 3/2005 |
| WO | WO 9940219 A1 * | 8/1999 |
| WO | WO 01/42498 | 6/2001 |

OTHER PUBLICATIONS

Okimoto et al. ("Improved PCR amplification of multiple specific alleles (PAMSA) using internally mismatched primers" Biotechniques. Jul. 1996:21(1):20-2, 24,26).*

Okano et al. ("Characteristics of selective polymerase chain reaction (PCR) using two-base anchored primers and improvement of its specificity" Electrophoresis. Dec. 1998;19(18):3071-8).*

Delrio-Lafreniere et al. ("Simultaneous allele-specific amplification: a strategy using modified primer-template mismatches for SNP detection—application to prothrombin 20210A (factor II) and factor V Leiden (1691A) gene mutations" Mol Digan. Sep. 2001;6(3):201-9).*

U.S. Appl. No. 11/333,352, filed Jan. 18, 2006, Yaku et al.
U.S. Appl. No. 11/203,417, filed Aug. 15, 2005, Yaku et al.
U.S. Appl. No. 11/471,646, filed Jun. 21, 2006, Yaku et al.
U.S. Appl. No. 11/363,953, filed Mar. 1, 2006, Yaku et al.
U.S. Appl. No. 11/489,582, filed Jul. 20, 2006, Yaku et al.
U.S. Appl. No. 11/488,633, filed Jul. 19, 2006, Yaku et al.
U.S. Appl. No. 11/489,583, filed Jul. 20, 2006, Yaku et al.
U.S. Appl. No. 11/633,587, filed Dec. 5, 2006, Yaku et al.
U.S. Appl. No. 11/633,584, filed Dec. 5, 2006, Yaku et al.
U.S. Appl. No. 11/607,907, filed Dec. 4, 2006, Yaku et al.
U.S. Appl. No. 11/488,635, filed Jul. 19, 2006, Yaku et al.
U.S. Office Action issued in corresponding U.S. Appl. No. 11/633,584, mailed Jun. 22, 2007.
U.S. Office Action issued in corresponding U.S. Appl. No. 11/471,646, mailed Jun. 26, 2007.
Delrio-Lafreniere et al., "Simultaneous Allele-specific Amplification: A Strategy Using Modified Primer-template Mismatches for SNP Detection-Application to Prothrombin 20210A (Factor II) and Factor V Leiden (1691A) Gene Mutations," Molecular Diagnosis vol. 6, No. 3, pp. 201-209, 2001, Minneapolis, Minnesota.

* cited by examiner

*Primary Examiner*—Kenneth R. Horlick
*Assistant Examiner*—Christopher M. Babic
(74) *Attorney, Agent, or Firm*—McDermott Will & Emery LLP

(57) ABSTRACT

An object of the present invention is to provide an allele specific primer which is accompanied by less possibility of the false positive and enables definite discrimination when a base immediately adjacent to on the 3' side of a target SNP base is G, while a base adjacent with one base spaced apart is T. According to the present invention, the 3' end base is designed to be the base corresponding to SNP; the second base from the 3' end to be T or G; the third base from the 3' end to be G or C; and the base sequence of from the fourth from the 3' end to the 5' end base to be completely complementary to the sequence of from a base three bases away from the target SNP base on the 3' side to a desired base.

7 Claims, 3 Drawing Sheets

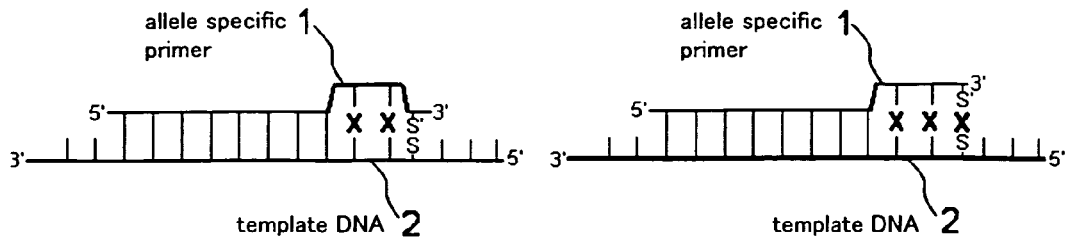

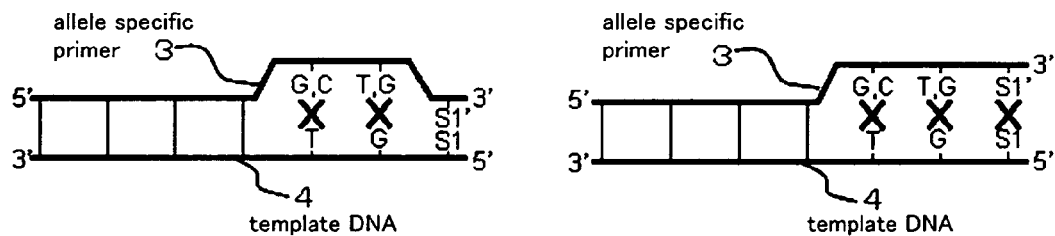

Fig. 2A    Fig. 2B

| S1: Prepare a double stranded DNA including a target DNA sequence so that a primer extension reaction can be carried out |
|---|
| S2: Carry out a primer extension reaction through adding the allele specific primer that meets the sequence requirements demonstrated in Embodiment 1, DNA polymerase, dNTPs, a buffer, and a desired salt as needed |
| S3: Analyze efficiency of the primer extension reaction in S2 |

Fig. 3

DISCRIMINATION METHOD OF TARGET BASE IN DNA, AND ALLELE SPECIFIC PRIMER USED IN THE METHOD OF THE SAME

BACKGROUND OF THE INVENTION

1. Field of the Invention

The present invention relates to a method of discriminating a target base carried by a DNA and an allele specific primer for use in the same.

2. Description of the Related Art

SNP is a polymorphism which occurs most frequently among gene polymorphisms, and is believed to appear in human genomes with an incidence of about 0.1%.

As a matter of fact, presence of SNPs of as many as over three million has been hitherto elucidated, suggesting that SNP may be very useful as a marker for genetic tests.

Investigations on relationship between SNPs and diseases carried out so far have revealed close relationship between diseases such as diabetes and hypertension, and SNP.

Known techniques for carrying out SNP discrimination include techniques in which a primer extension reaction (including PCR reaction) by an allele specific primer is utilized. A primer which yields a marked difference in efficiency of the primer extension reactions depending on the base type at targeted SNP is referred to as the allele specific primer. Therefore, the base type at the target SNP can be readily specified, for example, by carrying out a PCR reaction using an allele specific primer, and analyzing the amount of the PCR product.

In general, allele specific primers are simple origo DNAs which are not anyhow modified especially.

For analysis of the amount of PCR product, so called general electrophoretic method may be used. Thus, SNP discrimination techniques with an allele specific primer may be referred to as being extremely advantageous in terms of cost, reaction time, convenience of operation and the like.

With respect to methods of analysis, in addition to the aforementioned electrophoretic method, detection by QCM or SPR is also enabled when a solid phase reaction is carried out.

More recently, methods of detecting PPi (pyrophosphate) that is a byproduct of a primer extension reaction utilizing a luciferase reaction have been also developed. Accordingly, approaches to simplification and acceleration of SNP discrimination with an allele specific primer have been elaborately attempted all over the world.

Sequence design of an allele specific primer is a very important factor for its ability to discriminate SNP.

In the most classical example, 3' end base corresponds to the target SNP base (i.e., complementary to any one of predicted base types at the target SNP), and other sequence is completely complementary to the target DNA sequence. However, in this case, problems of the false positive may be raised unless reaction conditions are strictly defined such as the reaction time and temperature, or concentration of dNTPs used in the reaction, as well as cycle number when a PCR method is employed. In other words, fundamentally, although a primer extension reaction must not be caused from a base corresponding to SNP of the primer 3' end when it is noncomplementary to the target SNP base of a sample, the reaction is caused in many cases.

In order to solve the aforementioned problems in connection with the false positive, several novel allele specific primers have been developed so far.

An allele specific primer proposed in US Patent Publication No. 2003/0049628 is a developed allele specific primer in which the 3' end base is a base corresponding to SNP, and the third base from the 3' end was intentionally made noncomplementary to a base adjacent to on the 3' side of the target SNP base with two bases apart.

US Patent Publication No. 2003/0148301 proposes an allele specific primer in which the second base from the 3' end is a base corresponding to SNP, and the third base from the 3' end base is intentionally made noncomplementary to a base adjacent to on the 3' side of the target SNP base. In this instance, KOD polymerase that is 3'→5' exo+polymerase is characteristically utilized.

US Patent Publication No. 2004/0197803 proposes an allele specific primer in which 3' end base is a base corresponding to SNP, and the second and the third bases from the 3' end are intentionally made noncomplementary to a base adjacent to on the 3' side of the target SNP base and a base adjacent with one base spaced apart, respectively. Among them, the allele specific primer proposed in US Patent Publication No. 2004/0197803 involves low possibility of the false positive, in particular.

More specifically, the allele specific primer disclosed in US Patent Publication No. 2004/0197803 which was designed as described above may construct a loop structure, as shown in FIGS. 1A and 1B, because only the second and the third bases from the 3' end are noncomplementary to the target DNA sequence (in the Figure, noncomplementary base pair is denoted by "x") when the base corresponding to SNP positioned to its 3' end (in the Figure, denoted by "S'") is complementary to the target SNP base (in the Figure, denoted by "S") (FIG. 1A). Consequently, the polymerase is efficiently bound to cause a primer extension reaction.

To the contrary, when the base corresponding to SNP positioned to its 3' end is noncomplementary to the target SNP base, all three bases at the 3' end become noncomplementary, and branched structure may be constructed (FIG. 1B). In this case, the primer extension reaction is hardly caused because binding efficiency of polymerase is believed to be extremely low. Therefore, the allele specific primer proposed in US Patent Publication No. 2004/0197803 shall involve extremely low possibility of the false positive as described above.

In addition, the following documents can be referred to as relevant documents to the present invention.

Japanese Patent Provisional Publication No. 2004-248635 discloses a PCR primer for identification of rice variety in which 3' end corresponds to the SNP site to be discriminated, and the third base from the 3' end is substituted from a sequence that is complementary to the template sequence to be annealed, with the substitution being G to A, A to C, T to G, or C to A.

Further, paragraph No. 0040 of Japanese Patent Provisional Publication No. 2004-248635 discloses that "In one aspect, the present invention provides a primer in which the first, the second, the third or the fourth base from the 3' end was substituted. This substitution may be just alone, or a combination of two or more. Preferably, only the third base from the 3' end is substituted. This substitution of the primer may be any arbitrary substitution, but is preferably a substitution of G to T, A to C, T to G, or C to A.".

SUMMARY OF THE INVENTION

The allele specific primer proposed in US Patent Publication No. 2004/0197803 exhibits extremely inferior efficiency of the primer extension reaction when the base corresponding to SNP positioned at its 3' end is noncomplementary to the target SNP base. Consequently, problems of the false positive may be resolved, thereby enabling accurate discrimination of SNP discrimination.

However, efficiency of the primer extension reaction in case where the base corresponding to SNP positioned at its 3' end is complementary to the target SNP base may vary depending on the second and the third base types from the 3' end, and the base type requirements of the target DNA corresponding thereto (more specifically, base type requirements of a base adjacent to on the 3' side of the target SNP base and a base adjacent with one base spaced apart).

More specifically, for example, when a base type at the target SNP in the target DNA sequence is A (adenine) or G (guanine), and a base type immediately adjacent to on the 3' side of the SNP base is C (cytosine), while a base type adjacent with one base spaced apart is T (thymine), 3' end base of the allele specific primer proposed in US Patent Publication No. 2004/0197803 shall be a base corresponding to SNP, and thus may be T (to be complementary to A) or C (to be complementary to G). On the other hand, the second and the third bases from its 3' end must be noncomplementary to the target DNA sequence, the second base should be any one of A, T or C, and the third base should be any one of T, G or C. Therefore, there exist 9 kinds of combination in total of the allele specific primer proposed in US Patent Publication No. 2004/0197803 with respect to the second and the third base types from its 3' end for one kind of target DNA sequence. From the perspective that any one is noncomplementary, these 9 kinds of allele specific primers are supposed to exhibit approximately the same efficiency upon SNP discrimination.

However, the present inventors found that certain allele specific primers among these 9 kinds of allele specific primers exhibit extremely high efficiency upon SNP discrimination in comparison with other allele specific primers. Thus, the present invention was accomplished.

Accordingly, an object of the present invention is to provide a method of discriminating a target base carried by a DNA which is accompanied by less possibility of the false positive and enables definite discrimination, and an allele specific primer for use in the same.

The present invention provides a method of discriminating a target base carried by a DNA, the method which comprises:

(1) a DNA elongation step comprising binding to the DNA an allele specific primer having at its 3' end a base that is complementary to a base predicted as the target base among 4 bases of A, T, G and C to cause a DNA elongation reaction, and (2) a discrimination step comprising examining efficiency of the DNA elongation to discriminate that the target is the same as the predicted base when the efficiency is high, or that the target base is distinct from the predicted base when the efficiency is low, wherein in the DNA, a base immediately adjacent to on the 3' end side of the target base is G, and a base adjacent with one base spaced apart is T, 3' end base of the allele specific primer is complementary to the base predicted to be the target base, the second base from the 3' end of the allele specific primer is T or G, the third base from the 3' end of the allele specific primer is any one of G or C, and a base sequence between the fourth base from the 3' end and the 5' end base of the allele specific primer complementarily binds to a base sequence between the base on the DNA corresponding to the fourth base from the 3' end of the allele specific primer and the base on the DNA corresponding to the 5' end base of the allele specific primer.

The DNA elongation reaction is preferably a primer extension reaction. The DNA elongation reaction is preferably a primer extension reaction realized solely on said allele specific primer.

In this case, the efficiency is preferably examined by determining the concentration of pyrophosphate produced by the primer extension reaction. Further, the concentration of pyrophosphate is preferably detected in terms of luminescence intensity.

It is also preferred that the DNA elongation reaction is a PCR reaction. More preferably, the DNA elongation reaction is a PCR reaction relied on a combination of said allele specific primer with the other different primer. In this case, the efficiency is preferably examined by measuring the concentration of the amplified DNA produced by the PCR reaction with an electrophoretic method.

The allele specific primer which may be used in the above method is also involved in an aspect of the present invention.

According to the present invention, a method of discriminating a target base carried by a DNA which is accompanied by less possibility of the false positive and enables definite discrimination of SNP is provided.

The foregoing object, other object, features and advantages of the present invention will be apparent from the following detailed description of the preferred embodiments with reference to the accompanying drawings.

BRIEF DESCRIPTION OF THE DRAWINGS

FIG. 1A is a schematic view illustrating a relationship between a template DNA 2 and an allele specific primer 1 according to conventional arts.

FIG. 1B is a schematic view illustrating a relationship between a template DNA 2 and an allele specific primer 1 according to conventional arts.

FIG. 2A is a schematic view illustrating a relationship between a template DNA 4 and an allele specific primer 3 according to the present invention.

FIG. 2B is a schematic view illustrating a relationship between a template DNA 4 and an allele specific primer 3 according to the present invention.

FIG. 3 is a flow chart of a method of discriminating SNP in Embodiment 2.

DETAILED DESCRIPTION OF THE PREFERRED EMBODIMENTS

Figure 4:
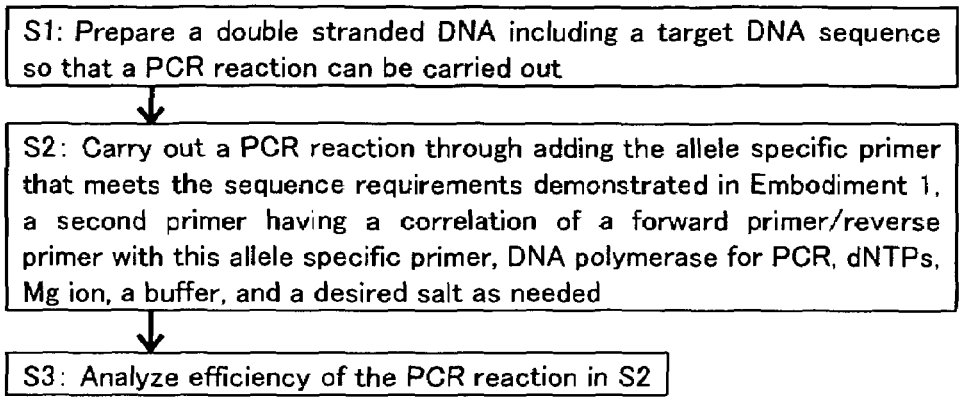
FIG. 4 is a flow chart of a method of discriminating SNP in Embodiment 3.

Hereinafter, embodiments of the present invention will be explained with reference to FIG. 2A to FIG. 4.

Embodiment 1

In this Embodiment 1, base type requirements for the allele specific primer according to the present invention will be explained with reference to FIGS. 2A and 2B.

In the present invention, as shown in FIGS. 2A and 2B, the target DNA sequence to be a subject includes the target SNP base present at the 5' end, the second base from the 5' end being G and the third base from the 5' end being T.

In order to facilitate understanding of the present invention, it is assumed that the target SNP base is present at the 5' end in FIGS. 2A and 2B. However, in general, the target SNP base may be present anywhere in the target DNA sequence, as shown in FIGS. 1A and 1B, and it is not necessary to exist at the 5' end of the target DNA sequence.

Because the 3' end base of the allele specific primer is a base corresponding to SNP, in case where there are two kinds of predicted base type at the target SNP (denoted as S1, S2 in FIGS. 2A and 2B), the 3' end base of the allele specific primer is designed such that complementarity is provided to either one of them. In FIGS. 2A and 2B, this base corresponding to SNP is denoted as S1' which is complementary to S1.

Moreover, the second base from the 3' end of the allele specific primer is T or G, and the third base from the 3' end is any one of G or C.

Base sequence between the fourth base from the 3' end and the 5' end base of the allele specific primer (hereinafter, may be referred to as "residual base sequence" or "residual base sequence of allele specific primer") is complementary and binds to the base sequence between the base on the target DNA corresponding to the fourth base from the 3' end of the allele specific primer and the base on the target DNA corresponding to the 5' end base of the allele specific primer (hereinafter, may be referred to as "residual base sequence" or "residual base sequence on the target DNA").

In FIGS. 2A and 2B, the base sequence of from the fourth base from the 3' end to the 5' end base of the allele specific primer is complementary to the base sequence of from the fourth base from the 5' end to the 3' end base in the target DNA sequence.

It is desired that the residual base sequence of the allele specific primer and the residual base sequence of the target DNA are completely complementary, but it is not necessarily completely complementary as long as any adverse effect is not exerted on the SNP discrimination.

According to the present invention, when the base corresponding to SNP of the allele specific primer is complementary to the target SNP base, relationship as shown in FIG. 2A is provided. To the contrary, when the base corresponding to SNP of the allele specific primer is noncomplementary to the target SNP base, relationship as shown in FIG. 2B is provided.

In FIGS. 2A and 2B (and FIGS. 1A and 1B), the reference sign "X" means that the two bases sandwiching the reference sign X therebetween are not bound. The two bases without the reference sign "X" sandwiched therebetween (for example, the base S1 and the base S1' in FIG. 1A and FIG. 2A) are bound.

When a DNA elongation reaction (i.e., typically a primer extension reaction or a PCR reaction) is carried out with the sequence requirements of such an allele specific primer and a target DNA using polymerase without 3' 5' exonuclease activity, the reaction proceeds very efficiently in case of FIG. 2A, while the reaction hardly proceeds in case of FIG. 2B.

The target SNP base carried by the DNA can be discriminated based on such difference in efficiency. More specifically, upon examination of the efficiency in the DNA elongation step, high efficiency leads to discrimination that the target SNP base is identical with the predicted base, while low efficiency leads to discrimination that the target SNP base is different from the predicted base.

Consequently, SNP discrimination is enabled which is accompanied by extremely low possibility of the false positive and is definite.

Embodiment 2

In this Embodiment 2, a method of discriminating SNP by carrying out a primer extension reaction using an allele specific primer according to the present invention will be explained.

As shown in FIG. 3, a double stranded DNA including a target DNA sequence is first prepared so that a primer extension reaction can be carried out. In the target DNA sequence requirements, the target SNP base is present at the 5' end, with the second base from the 5' end being G and the third base from the 5' end being T, similarly to Embodiment 1.

Therefore, the complementary chain sequence of the target DNA sequence has its 3' end base being complementary to the target SNP base, with the second base from the 3' end being C and the third base from the 3' end being A.

The double stranded DNA that meets such sequence requirements is prepared to provide the state to permit the primer extension reaction to be carried out as described above. Thus, a primer extension reaction may be carried out through adding the allele specific primer that meets the sequence requirements demonstrated in Embodiment 1, DNA polymerase, dNTPs, a buffer, and a desired salt as needed.

Step of the primer extension reaction may be conducted by any known procedure, which may be specifically, as follows.

That is, the aforementioned double stranded DNA is first stood under a high temperature condition for allowing denaturation, followed by lowering of the temperature such that binding of the allele specific primer according to the present invention with the target DNA sequence is permitted. Thereafter, the temperature condition may be set to allow the DNA polymerase to execute an elongation reaction.

Consequently, when the base corresponding to SNP positioned at the 3' end of the allele specific primer is complementary to the target SNP base, the primer extension reaction with this allele specific primer can be efficiently perfected. To the contrary, when the base corresponding to SNP positioned at the 3' end of the allele specific primer is noncomplementary to the target SNP base, efficiency of the primer extension reaction with this allele specific primer is significantly poor. Therefore, efficiency of the primer extension reaction may be examined during or following this primer extension reaction by measuring the amount of pyrophosphate released as a result of the primer extension reaction, or the like. Accordingly, SNP discrimination is enabled which is accompanied by less possibility of the false positive and is definite.

Procedure for examining efficiency of the primer extension reaction is not limited to the method of measuring the amount of pyrophosphate.

For example, efficiency of the primer extension reaction may be examined by carrying out the aforementioned primer extension reaction in the state in which a 5' end area of the allele specific primer according to the present invention is immobilized on a crystal oscillator, and monitoring the primer extension reaction through analyzing change in the oscillation frequency.

Alternatively, efficiency of the primer extension reaction may be examined by carrying out the aforementioned primer extension reaction in the state in which a 5' end area of the allele specific primer according to the present invention is immobilized on a gold surface, and monitoring the primer extension reaction through analyzing the surface plasmon resonance (SPR) phenomenon.

Any procedure is permitted as long as efficiency of the primer extension reaction can be examined.

Specific procedure for carrying out the primer extension reaction is not limited to those described above. More specifically, all necessary reagents are previously mixed into a reaction mixture to execute the primer extension reaction in the procedure described above, however, for example, a buffer solution in which the double stranded DNA including a target DNA sequence and the allele specific primer dissolved therein (a desired salt may be added as needed) may be prepared first, and then a denaturation step at a high temperature and binding to the target DNA sequence with the allele specific primer may be allowed, followed by serially adding DNA polymerase and dNTPs thereto to execute the reaction. Thus, any step may be permitted as long as the primer extension reaction can be perfected.

Also, in case where the DNA including a target DNA sequence is originally single stranded, step of standing under a high temperature condition intending to allow the double stranded DNA to be denatured is not required unlike in the case of the double stranded DNA sequence.

However, the single stranded DNA and the allele specific primer must be conditioned to provide a state in which both of them are sufficiently dissociated intending to control their binding reaction. Therefore, it is preferred that a step of standing them under a high temperature condition is conducted prior to the binding step of the allele specific primer and the target DNA sequence.

The DNA polymerase herein preferably has week or no 3'→5' exonuclease activity, which may result in more accurate SNP discrimination. Furthermore, the DNA polymerase can be exposed to a high temperature depending on the procedure of the primer extension reaction as described above. In such a case, heat resistance enzyme must be used such as e.g., one for use in PCR, however, it is not particularly necessary in case where the primer extension reaction is carried out by a procedure to avoid exposure of the enzyme to such a high temperature.

Examples of the method of measuring the amount of pyrophosphate include those proposed in Nucleic Acids Research, 2001, Vol. 29, No. 19 e93, WO 03/078655 A1, Japanese Patent Provisional Publication No. 2004-141158 and the like. However, the method is not limited thereto, but any method capable of measuring pyrophosphate is permitted.

Embodiment 3

In this Embodiment 3, a method of discriminating SNP by carrying out PCR using the allele specific primer according to the present invention will be explained.

As shown in FIG. 4, a double stranded DNA including a target DNA sequence is first prepared so that a PCR reaction can be carried out. In the target DNA sequence requirements then, the target SNP base is present at the 5' end, with the second base from the 5' end being G and the third base from the 5' end being T, similarly to Embodiment 1.

Therefore, the complementary chain sequence of the target DNA sequence has its 3' end base being complementary to the target SNP base, with the second base from the 3' end being C and the third base from the 3' end being A.

The double stranded DNA that meets such sequence requirements is prepared to give the state to permit the PCR reaction to be carried out as described above. Thus, a PCR reaction may be carried out through adding the allele specific primer that meets the sequence requirements demonstrated in Embodiment 1, a second primer having a correlation of a forward primer/reverse primer with this allele specific primer, DNA polymerase for PCR, dNTPs, Mg ion, a buffer, and a desired salt as needed.

Consequently, when the base corresponding to SNP positioned at the 3' end of the allele specific primer is complementary to the target SNP base, template DNA in the region sandwiched between this allele specific primer and the second primer can be efficiency amplified. To the contrary, when the base corresponding to SNP positioned at the 3' end of the allele specific primer is noncomplementary to the target SNP base, template DNA in the region sandwiched between this allele specific primer and the second primer is hardly amplified. Accordingly, SNP discrimination is enabled which is accompanied by less possibility of the false positive and is definite through determination of the amount of amplification of this template DNA by a method such as electrophoresis following the PCR reaction.

Alternatively, the amount of pyrophosphate released as a result of the PCR reaction may be measured during or following the PCR reaction as described above. Also in this case, SNP discrimination is enabled which is accompanied by less possibility of the false positive and is definite.

The DNA polymerase for PCR described above preferably has week or no 3'→5' exonuclease activity.

Method of measuring the amount of amplification of the template DNA is not particularly limited, but a method other than the aforementioned electrophoretic method is permitted.

Examples of the method of measuring the amount of pyrophosphate include those proposed in Nucleic Acids Research, 2001, Vol. 29, No. 19 e93, WO 03/078655 A1, Japanese Patent Provisional Publication No. 2004-141158 and the like. However, the method is not limited thereto, but any method capable of measuring pyrophosphate is permitted.

Embodiment 4

In this Embodiment 4, a kit for discriminating SNP including the allele specific primer according to the present invention will be explained.

Users may carry out a primer extension reaction and a reaction for measuring pyrophosphate using the kit for discriminating SNP explained in this section, thereby enabling discrimination of the base type at the target SNP in each sample with low possibility of the false positive and in an accurate manner.

The kit for discriminating SNP according to this Embodiment 4 comprises an allele specific primer reagent tube including the allele specific primer according to the present invention as demonstrated in Embodiment 1 for the target DNA sequence, a DNA polymerase reagent tube including DNA polymerase, a buffer reagent tube including a buffer to which a desired salt is added as needed, a dNTPs reagent tube including dNTPs, and a pyrophosphate reagent tube including a reagent for measuring pyrophosphate.

Therefore, the users first prepare a single stranded DNA or double stranded DNA sample including each target DNA sequence to give the state to permit the primer extension reaction to be carried out, and thereafter may carry out the primer extension reaction according to the method explained in Embodiment 2 using the allele specific primer included in the allele specific primer reagent tube, the DNA polymerase included in the DNA polymerase reagent tube, the buffer included in the buffer reagent tube, and dNTPs included in the dNTPs reagent tube.

Pyrophosphate released into the reaction mixture during the process of the primer extension reaction may be measured using a reagent for measuring pyrophosphate included in the aforementioned pyrophosphate reagent tube.

Accordingly, discrimination of the base type at the target SNP is enabled with low possibility of the false positive and in an accurate manner.

The reagents for measuring pyrophosphate are not particularly limited as long as pyrophosphate can be measured, but ATP sulfurylase for converting pyrophosphate into ATP, luciferin for executing a luminescence reaction (wavelength: 520 nm) through reacting with ATP, and luciferase that catalyzes the reaction may be included, when a luminescence reaction by means of luciferase is used as demonstrated in Nucleic Acids Research, 2001, Vol. 29, No. 19 e93. These may be in the state of being admixed in one tube, or they may be included in separate tubes, respectively. In any case, the users can optically measure pyrophosphate released in the process of the aforementioned primer extension reaction using these reagents for measuring pyrophosphate according to the method disclosed in Nucleic Acids Research, 2001, Vol. 29, No. 19 e93.

Additionally, in this instance, because DATP remained unreacted in the primer extension reaction reacts with luciferin, a tube including an enzyme for decomposing the unreacted dATP may preferably be included in a part of the kit. It is preferred that this enzyme is added to the primer extension reaction liquid before the reaction with luciferase as described above, or before the reaction for converting pyrophosphate into ATP, thereby executing the DATP decomposing reaction.

With respect to the reagent for measuring pyrophosphate, when the electrochemical measurement method of pyrophosphate illustrated in WO 03/078655A1 is used, pyrophosphatase for hydrolyzing pyrophosphate into phosphoric acid, GAP (glyceraldehyde 3-phosphate) and NAD that react with this phosphoric acid, GAPDH that catalyzes the reaction of this phosphoric acid-GAP-NAD (glyceraldehyde 3-phosphate dehydrogenase), an electron-transfer mediator (oxidized form) that reacts with NADH obtained by this reaction of phosphoric acid-GAP-NAD, and diaphorase that catalyzes the reaction of the NADH and the electron-transfer mediator may be included. These may be in the state of being admixed in one tube, or they may be included in separate tubes, respectively. In any case, the users can electrochemically measure pyrophosphate released in the process of the aforementioned primer extension reaction using the reagents for measuring pyrophosphate according to the method disclosed in WO 03/078655A1.

With respect to the reagent for measuring pyrophosphate, when the electrochemical measurement method illustrated in Japanese Patent Provisional Publication No. 2004-141158 is used, a membrane comprising $H^+$-PPase ($H^+$-pyrophosphatase) that hydrolyzes pyrophosphate into phosphoric acid and transports $H^+$, and a dye stuff that exhibits altered optical characteristics depending on the $H^+$ concentration may be included. These may be in the state of being admixed in one tube, or may be included in separate tubes, respectively. In any case, the users can optically measure pyrophosphate released in the process of the aforementioned primer extension reaction using these reagents for measuring pyrophosphate according to the method disclosed in Japanese Patent Provisional Publication No. 2004-141158.

In connection with the method of measuring pyrophosphate, a number of methods other than those demonstrated herein have been known. Therefore, as a matter of course, the reagents for measuring pyrophosphate are not limited to those demonstrated herein, but any constitution may be permitted which includes all or a part of reagents required for the measurement of pyrophosphate.

In stead of the reagent for measuring pyrophosphate, a constitution including a fluorescence indicator that binds to a double stranded DNA such as SYBR$^{(R)}$ Green I in the kit of this Embodiment 4 may be permitted.

More specifically, when the primer extension reaction is allowed in the presence of a fluorescence indicator that binds to a double stranded DNA typified by SYBR$^{(R)}$ Green I, process of the primer extension reaction can be analyzed in real time by monitoring the fluorescence. SNP discrimination can be performed based on the results of this analysis.

The fluorescence indicator that binds to a double stranded DNA typified by SYBR$^{(R)}$ Green I may be included in one tube alone, or may be constituted to be included in the buffer reagent tube or the like. Accordingly, the kit may be constituted to permit this fluorescence indicator to be mixed in the primer extension reaction liquid.

Similarly, in stead of the reagent for measuring pyrophosphate, a constitution including Taq Man probe in the kit of this Embodiment 4 may be permitted. In other words, when Taq Man probe is designed to bind to a desired region in the sequence where the primer extension reaction proceeds, process of the primer extension reaction can be analyzed in real time by monitoring the fluorescence depending on this Taq Man probe. Accordingly, SNP discrimination can be performed based on the results of this analysis.

The Taq Man probe designed in such a manner may be included in one tube alone, or may be constituted to be included in the buffer reagent tube or the like. Thus, the kit may be constituted to permit the Taq Man probe to be mixed in a primer extension reaction liquid.

The aforementioned DNA polymerase herein preferably has week or no 3'→5' exonuclease activity for achieving more accurate SNP discrimination. In addition, it is more preferred that the DNA polymerase is heat resistant.

Embodiment 5

In this Embodiment 5, a kit for discriminating SNP including the allele specific primer according to the present invention will be explained.

Users may carry out a PCR reaction using the kit for discriminating SNP explained in this section, thereby enabling discrimination of the base type at the target SNP in each sample with low possibility of the false positive and in an accurate manner.

The kit for discriminating SNP according to this Embodiment 5 comprises a primer reagent tube including the allele specific primer according to the present invention as demonstrated in Embodiment 1 for the target DNA sequence and a second primer having a correlation of a forward primer/reverse primer with this allele specific primer, a DNA polymerase reagent for PCR tube including DNA polymerase for PCR, a buffer reagent tube including a buffer to which Mg ion and a desired salt are added as needed, and a dNTPs reagent tube including dNTPs.

Therefore, the users first prepare a double stranded DNA sample including each target DNA sequence to give the state to permit the PCR reaction to be carried out, and thereafter may carry out the PCR reaction according to the method explained in Embodiment 3 using the allele specific primer and the second primer included in the primer reagent tube, the DNA polymerase for PCR included in the DNA polymerase reagent for PCR tube, the buffer included in the buffer reagent tube, and dNTPs included in the dNTPs reagent tube.

It is more preferred that the kit according to this Embodiment 5 includes a reagent for examining efficiency of the PCR reaction. Examples of the reagent for examining the efficiency of the PCR reaction include, similarly to Embodiment 3, the reagents for measuring pyrophosphate, fluorescence indicators that bind to a double stranded DNA such as SYBR$^{(R)}$ Green I, and Taq Man probe.

The reagent for measuring pyrophosphate can measure pyrophosphate released into the reaction liquid during the PCR reaction. Therefore, based on the measurement results, discrimination of the base type at the target SNP is enabled with low possibility of the false positive and in an accurate manner. Types of the reagent for measuring pyrophosphate are similar to those in Embodiment 4, which may be constituted to include all or a part of the reagents required for the measurement of pyrophosphate.

In connection with the fluorescence indicator that binds to a double stranded DNA such as SYBR$^{(R)}$ Green I, or Taq Man probe, the process of the PCR reaction can be monitored in real time by carrying out the PCR reaction in the presence of the same. Thus, discrimination of the base type at the target SNP is enabled with low possibility of the false positive and in an accurate manner based on the results.

Therefore, these may be included in one tube alone, or may be constituted to be included in the buffer reagent tube or the like. Accordingly, the kit may be constituted to permit these reagents to be mixed in the PCR reaction liquid.

The allele specific primer according to the present invention, methods of discriminating SNP using this allele specific primer, kits for discriminating SNP including this allele specific primer were explained in the foregoings by way of Embodiments 1 to 5.

These are not particularly limited to SNP, but exactly similar effects may be achieved as a matter of course, also with respect to discrimination of difference in single base due to mutation, or discrimination of difference in single base caused by artificial mutation at a certain particular base.

EXAMPLES

More specific Examples of the present invention will be described below.

Example 1

In this Example 1, discrimination of the target base type in λDNA was carried out by a primer extension reaction using the allele specific primer according to the present invention.

More specifically, a mutant type λDNA-6965-GC was first produced by artificially substituting a T/A base pair at position 6965 in λDNA (manufactured by Takara Bio Inc.) to a G/C base pair.

Then discrimination of substitution of the base pair was performed using three primers of:

5'-CAACACGATGGTGCTGGGGAACGTT-3' (λ-GTT/SEQ ID No.1),

5'-CAACACGATGGTGCTGGGGAACGGT-3' (λ-GGT/SEQ ID No.2),

5'-CAACACGATGGTGCTGGGGAACCTT-3' (λ-CTT/SEQ ID No.3), and

5'-CAACACGATGGTGCTGGGGAACCGT-3' (λ-CGT/SEQ ID No.4).

The above four primers are referred to as λ-GTT, λ-GGT, λ-CTT and λ-CGT in this order.

The 3' end base T of the above four primers is complementary to the 5' end base A of 5'-AGTGTTCCCCAGCACCATCGTGTTG-3'(Antisense strand of SEQ ID No.5) among double stranded DNA sequences of 5'-CAACACGATGGTGCTGGGGAACACT-3'/5'-AGTGTTCCCCAGCACCATCGTGTTG-3'(SEQ ID No.5) consisting of positions 6941 to 6965 of the wild type λDNA.

The second base T (λ-GTT and λ-CTT) or G (λ-GGT and λ-CGT) from the 3' end of the above four primers is in a noncomplementary relation of T/G or G/G, to the second base G from the 5' end of 5'-AGTGTTCCCCAGCACCATCGTGTTG-3'(SEQ ID No.5), similarly.

The third base G (λ-GTT and λ-GGT) or C (λ-CTT and λ-CGT) from the 3' end of the above four primers is in a noncomplementary relation of G/T or C/T, to the third base T from the 5' end of 5'-AGTGTTCCCCAGCACCATCGTGTTG-3'(SEQ ID No.5), similarly.

The sequence of from the fourth base from the 3' end to the 5' end base of the above four primers is completely complementary, to sequence of from the fourth base from the 5' end to the 3' end base of 5'-AGTGTTCCCCAGCACCATCGTGTTG-3'(SEQ ID No.5), similarly.

On the other hand, three bases at the 3' end of the above four primers are noncomplementary to three bases at the 5' end of 5'-CGTGTTCCCCAGCACCATCGTGTTG-3'(Antisense strand of SEQ ID No.6) among the double stranded DNA sequences of 5'-CAACACGATGGTGCTGGGGAACACG-3'/5'-CGTGTTCCCCAGCACCATCGTGTTG-3'(SEQ ID No.6) consisting of positions 6941 to 6965 of the mutant type λDNA-6965-GC (mutation introduced site underlined).

As a reverse primer, a DNA consisting of 5'-GAATCACGGTATCCGGCTGCGCTGA-3'(SEQ ID No.7) was used.

This reverse primer is completely complementary to 5'-TCAGCGCAGCCGGATACCGTGATTC-3' (Sense strand of SEQ ID No.8) among the double stranded DNA sequences of 5'-TCAGCGCAGCCGGATACCGTGATTC-3'(SEQ ID No. 8)/5'-GAATCACGGTATCCGGCTGCGCTGA-3' consisting of positions 7406 to 7430 of the λDNA.

Provided that a PCR reaction with the aforementioned four primers favorably proceeds, a DNA amplification product of 490 bp will be obtained.

The experiment was conducted as follows.

First, 20 µL of a reaction solution was prepared containing:

2 µL of an enzyme mixture of Light Cycler-FastStart DNA Master SYBR Green I kit (manufactured by Roche Diagnostics), 10 µg/mL wild type λDNA or mutant type λDNA-6965-GC described above, 1 µM of any one of λ-GTT, λ-GGT, λ-CTT or λ-CGT, 1 µM reverse primer described above, and 1.6 mM $MgCl_2$.

This reaction solution was subjected to a PCR reaction using LightCycler that is a thermal cycler manufactured by Roche Diagnostics, under the condition of denaturation step: 94° C., 10 sec; annealing step: 58° C., 10 sec; extension step: 72° C., 10 sec; and cycle number: 20 cycles.

Results of each PCR reaction were analyzed using Bioanalyzer 2100 that is a system for DNA electrophoresis manufactured by Agilent Technologies Inc.

Figure 5:
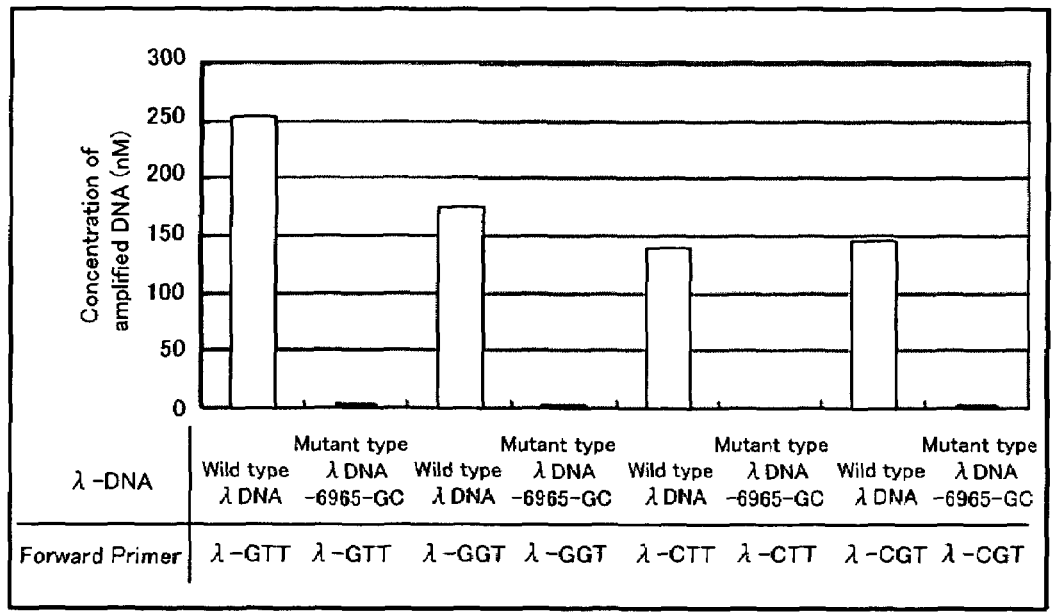
FIG. 5 is a graph presenting experimental results in Example 1.

Results of the analysis are illustrated in FIG. 5.

These results are shown by concentration (nM) of the target DNA fragment following each PCR reaction.

According to these results, in every case where any one of the aforementioned λ-GTT, λ-GGT, λ-CTT or λ-CGT was used, the target DNA fragment was scarcely detected in case of the mutant type λDNA-6965-GC.

To the contrary, in every case of the wild type λDNA, concentration of the target DNA fragment was equal to or greater than 50 nM.

Accordingly, it is concluded that the difference in single base in this Example could be definitely discriminated by carrying out a PCR reaction using the aforementioned λ-GTT, λ-GGT, λ-CTT or λ-CGT as a forward primer.

Comparative Example 1

In this Comparative Example 1, discrimination was attempted as a comparative experiment of the above Example 1 on difference in single base of the wild type λDNA of the above Example 1 and the mutant type λDNA-6965-GC using the following five primers.

More specifically, similar experiment to Example 1 was conducted using five primers consisting of the sequence of 5'-CAACACGATGGTGCTGGGGAACTAT-3'  (λ-TAT/SEQ ID No.9), 5'-CAACACGATGGTGCTGGGGAACTTT-3'  (λ-TTT/SEQ ID No.10), 5'-CAACACGATGGTGCTGGGGAACTGT-3'  (λ-TGT/SEQ ID No.11), 5'-CAACACGATGGTGCTGGGGAACGAT-3'  (λ-GAT/SEQ ID No.12), and 5'-CAACACGATGGTGCTGGGGAACCAT-3'  (λ-CAT/SEQ ID No.13).

These five primers are referred to as λ-TAT, λ-TTT, λ-TGT, λ-GAT and λ-CAT in this order.

In these sequences, similarly to λ-GTT, λ-GGT, λ-CTT and λ-CGT used in Example 1, the 3' end base (T) of these sequences are complementary to the 5' end base (A) of 5'-AGTGTTCCCCAGCACCATCGTGTTG-3'(SEQ ID No.5).

The second and the third bases from the 3' end of these sequences are noncomplementary to the second and the third bases from the 5' end of 5'-AGTGTTCCCCAGCACCATCGTGTTG-3'(SEQ ID No.5).

The residual sequence is completely complementary to the residual sequence of 5'-AGTGTTCCCCAGCACCATCGTGTTG-3'(SEQ ID No.5).

Figure 6:
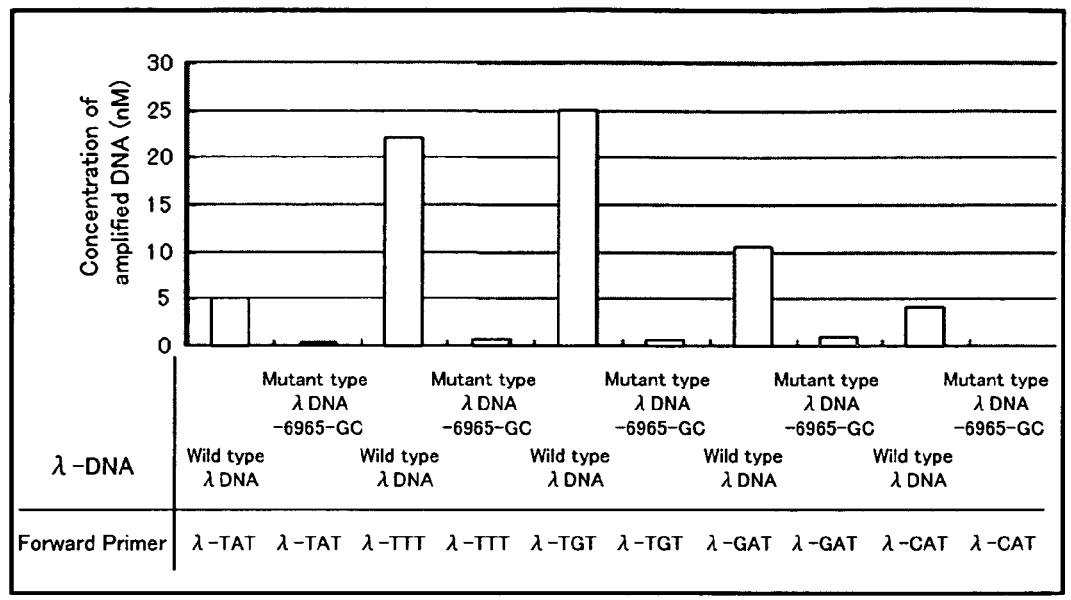
FIG. 6 is a graph presenting experimental results in Comparative Example 1.

Results of the analysis are illustrated in FIG. 6.

These results are shown by concentration (nM) of the target DNA fragment following each PCR reaction.

According to these results, in every case where any one of the aforementioned λ-TAT, λ-TTT, λ-TGT, λ-GAT or λ-CAT was used, the target DNA fragment was scarcely detected in case of the mutant type λDNA-6965-GC.

To the contrary, in every case of the wild type λDNA, concentration of the target DNA fragment was equal to or greater than 4 nM.

It is shown that a single base difference between the wild type λDNA and the mutant type λDNA-6965-GC can be discriminated by using λ-TAT, λ-TTT, λ-TGT, λ-GAT or λ-CAT. However, when the wild type λDNA is used as a template, the concentrations of amplification products are apparently lower for λ-GTT, λ-GGT, λ-CTT and λ-CGT (note the scales of the vertical axes in FIGS. 5 and 6). This implies that λ-GTT, λ-GGT, λ-CTT and λ-CGT are better discriminators.

As is seen from these Example 1 and Comparative Example 1, extremely high discrimination capability can be attained when a base immediately adjacent to on the 3' end side of the target SNP base is G; a base adjacent with one base spaced apart is T; the second base from the 3' end of the allele specific primer is T or G; and the third base is any one of G or C.

Example 2

In this Example 2, discrimination of the target base type in λDNA was carried out by a PCR reaction using the allele specific primer according to the present invention.

The following three mutant type λDNAs was first produced:

1. Mutant Type λDNA-7248-GC

A mutant type λDNA produced by artificially substituting an A/T base pair at position 7248 in wild type λDNA to a G/C base pair;

2. Mutant Type λDNA-7064-AT

A mutant type λDNA produced by artificially substituting a C/G base pair at position 7064 in wild type λDNA to an A/T base pair;

3. Mutant Type λDNA-7011-AT

A mutant type λDNA produced by artificially substituting a G/C base pair at position 7011 in wild type λDNA to an A/T base pair.

Then following three patterns of discrimination of substitution of the base pair was performed:

Discrimination No. 1

Discrimination between an A/T base pair at position 7248 in wild type λDNA and a G/C base pair at position 7248 in mutant type λDNA-7248-GC;

Discrimination No. 2

Discrimination between a C/G base pair at position 7064 in wild type λDNA and an A/T base pair at position 7064 in mutant type λDNA-7064-AT;

Discrimination No. 3

Discrimination between a G/C base pair at position 7011 in wild type λDNA and an A/T base pair at position 7011 in mutant type λDNA-7011-AT.

Then discrimination of substitution of the base pair was performed using following primers as a forward primer:

Primers Used for Discrimination No. 1

5'-GTCTCCGCTCGCTGGGTGATAA-3'  (λ1-TAA/SEQ ID No.14)

5'-GTCTCCGCTCGCTGGGTGATTA-3' (λ1-TTA/SEQ ID No.15)

5'-GTCTCCGCTCGCTGGGTGATGA-3'  (λ1-TGA/SEQ ID No.16)

5'-GTCTCCGCTCGCTGGGTGAGAA-3'  (λ1-GAA/SEQ ID No.17)

5'-GTCTCCGCTCGCTGGGTGAGTA-3'  (λ1-GTA/SEQ ID No.18)

5'-GTCTCCGCTCGCTGGGTGAGGA-3' (λ1-GGA/SEQ ID No.19)

5'-GTCTCCGCTCGCTGGGTGACAA-3' (λ1-CAA/SEQ ID No.20)

5'-GTCTCCGCTCGCTGGGTGACTA-3' (λ1-CTA/SEQ ID No.21)

5'-GTCTCCGCTCGCTGGGTGACGA-3' (λ1-CGA/SEQ ID No.22)

The 3' end base A of the above nine primers is complementary to the 5' end base T of 5'-TGTTCACCCAGC-GAGCGGAGAC-3'(Antisense strand of SEQ ID No.23) among the double stranded DNA sequences of 5'-GTCTC-CGCTCGCTGGGTGAACA-3'/5'-TGTTCACCCAGC-GAGCGGAGAC-3, (SEQ ID No.23) consisting of positions 7227 to 7248 of the wild type λDNA.

The second and the third bases from the 3' end of the above nine primers are all different, but they are in a noncomplementary relation, to the second and the third bases 5'-GT-3' from the 5' end of 5'-TGTTCACCCAGC-GAGCGGAGAC-3'(SEQ ID No.23), respectively.

The sequence of from the fourth base from the 3' end to the 5' end base of the above nine primers is completely complementary, similarly, to sequence of from the fourth base from the 5' end to the 3' end base of 5'-TGTTCAC-CCAGCGAGCGGAGAC-3'(SEQ ID No.23).

On the other hand, three bases at the 3' end of the above nine primers are noncomplementary to three bases at the 5' end of 5'-CGTTCACCCAGCGAGCGGAGAC-3'(Antisense strand of SEQ ID No.24) among the double stranded DNA sequences of 5'-GTCTCCGCTCGCTGGGTGAACG-3'/5'-CGTTCACCCAGCGAGCGGAGAC-3'(SEQ ID No.24) consisting of positions 7227 to 7248 of the mutant type λDNA-7248-GC (mutation introduced site underlined).

Primers Used for Discrimination No. 2

5'-CCGTTACCCGAAAAACTGGGTGTAC-3' (λ2-TAC/SEQ ID No.25)

5'-CCGTTACCCGAAAAACTGGGTGTTC-3' (λ2-TTC/SEQ ID No.26)

5'-CCGTTACCCGAAAAACTGGGTGTGC-3' (λ2-TGC/SEQ ID No.27)

5'-CCGTTACCCGAAAAACTGGGTGGAC-3' (λ2-GAC/SEQ ID No.28)

5'-CCGTTACCCGAAAAACTGGGTGGTC-3' (λ2-GTC/SEQ ID No.29)

5'-CCGTTACCCGAAAAACTGGGTGGGC-3' (λ2-GGC/SEQ ID No.30)

5'-CCGTTACCCGAAAAACTGGGTGCAC-3' (λ2-CAC/SEQ ID No.31)

5'-CCGTTACCCGAAAAACTGGGTGCTC-3' (λ2-CTC/SEQ ID No.32)

5'-CCGTTACCCGAAAAACTGGGTGCGC-3' (λ2-CGC/SEQ ID No.33)

The 3' end base C of the above nine primers is complementary to the 5' end base G of 5'-GGTCAC-CCAGTTTTTCGGGTAACGG-3'(Antisense strand of SEQ ID No.34) among the double stranded DNA sequences of 5'-CCGTTACCCGAAAAACTGGGTGACC-3'/5'-GGT-CACCCAGTTTTTCGGGTAACGG-3'(SEQ ID No.34) consisting of positions 7040 to 7064 of the wild type λDNA.

The second and the third bases from the 3' end of the above nine primers are all different, but they are in a noncomplementary relation, to the second and the third bases 5'-GT-3' from the 5' end of 5'-GGTCAC-CCAGTTTTTCGGGTAACGG-3'(SEQ ID No.34), respectively.

The sequence of from the fourth base from the 3' end to the 5' end base of the above nine primers is completely complementary, similarly, to sequence of from the fourth base from the 5' end to the 3' end base of 5'-GGTCAC-CCAGTTTTTCGGGTAACGG-3'(SEQ ID No.34).

On the other hand, three bases at the 3' end of the above nine primers are noncomplementary to three bases at the 5' end of 5'-TGTCACCCAGTTTTTCGGGTAACGG-3'(Antisense strand of SEQ ID No.35) among the double stranded DNA sequences of 5'-CCGTTACCCGAAAAACTGGGTGACA-3'/5'-TGTCACCCAGTTTTTCGGGTAACGG-3'(SE Q ID No.35) consisting of positions 7040 to 7064 of the mutant type λDNA-7064-AT (mutation introduced site underlined).

Primers Used for Discrimination No. 3

5'-GCTGCATTCAGGATGCGGTAG-3' (λ3-TAG/SEQ ID No.36)

5'-GCTGCATTCAGGATGCGGTTG-3' (λ3-TTG/SEQ ID No.37)

5'-GCTGCATTCAGGATGCGGTGG-3' (λ3-TGG/SEQ ID No.38)

5'-GCTGCATTCAGGATGCGGGAG-3' (λ3-GAG/SEQ ID No.39)

5'-GCTGCATTCAGGATGCGGGTG-3' (λ3-GTG/SEQ ID No.40)

5'-GCTGCATTCAGGATGCGGGGG-3' (λ3-GGG/SEQ ID No.41)

5'-GCTGCATTCAGGATGCGGCAG-3' (λ3-CAG/SEQ ID No.42)

5'-GCTGCATTCAGGATGCGGCTG-3' (λ3-CTG/SEQ ID No.43)

5'-GCTGCATTCAGGATGCGGCGG-3' (λ3-CGG/SEQ ID No.44)

The 3' end base G of the above nine primers is complementary to the 5' end base C of 5'-CGTCCGCATCCT-GAATGCAGC-3'(Antisense strand of SEQ ID No.45) among the double stranded DNA sequences of 5'-GCTG-CATTCAGGATGCGGACG-3'/5'-CGTCCGCATCCT-GAATGCAGC-3'(SEQ ID No.45) consisting of positions 6991 to 7011 of the wild type λDNA.

The second and the third bases from the 3' end of the above nine primers are all different, but they are in a noncomplementary relation, to the second and the third bases 5'-GT-3' from the 5' end of 5'-CGTCCGCATCCT-GAATGCAGC-3'(SEQ ID No.45), respectively.

The sequence of from the fourth base from the 3' end to the 5' end base of the above nine primers is completely complementary, similarly, to sequence of from the fourth base from the 5' end to the 3' end base of 5'-CGTCCG-CATCCTGAATGCAGC-3'(SEQ ID No.45).

On the other hand, three bases at the 3' end of the above nine primers are noncomplementary to three bases at the 5' end of 5'-TGTCCGCATCCTGAATGCAGC-3'(Antisense strand of SEQ ID No.46) among the double stranded DNA sequences of 5'-GCTGCATTCAGGATGCGGACA-3'/5'-TGTCCGCATCCTGAATGCAGC-3'(SEQ ID No.46) consisting of positions 6991 to 7011 of the mutant type λDNA-7011-AT (mutation introduced site underlined).

Similarly to Example 1 and Comparative Example 1, a DNA consisting of 5'-GAATCACGGTATCCGGCT-GCGCTGA-3'(SEQ ID No.7) was used as a reverse primer in any one of Discrimination 1, Discrimination 2 and Discrimination 3.

The following PCR reaction solutions were prepared for Discrimination 1, Discrimination 2 and Discrimination 3 using the above-described forward and reverse primers.

PCR Reaction Solution Used for Discrimination No. 1

First, 20 μL of a reaction solution was prepared containing:

2 μL of an enzyme mixture of Light Cycler-FastStart DNA Master SYBR Green I kit (manufactured by Roche Diagnostics), 10 μg/mL wild type λDNA or mutant type λDNA-7248-GC described above, 1 μM of any one of the above primers used for discrimination No. 1, 1 μM reverse primer described above, and 1.6 mM $MgCl_2$.

PCR Reaction Solution Used for Discrimination No. 2

First, 20 μL of a reaction solution was prepared containing:

2 μL of an enzyme mixture of Light Cycler-FastStart DNA Master SYBR Green I kit (manufactured by Roche Diagnostics), 10 μg/mL wild type λDNA or mutant type λDNA-7064-AT described above, 1 μM of any one of the above primers used for discrimination No. 2, 1 μM reverse primer described above, and 1.6 mM $MgCl_2$.

PCR Reaction Solution Used for Discrimination No. 3

First, 20 μL of a reaction solution was prepared containing:

2 μL of an enzyme mixture of Light Cycler-FastStart DNA Master SYBR Green I kit (manufactured by Roche Diagnostics), 10 μg/mL wild type λDNA or mutant type λDNA-7011-AT described above, 1 μM of any one of the above primers used for discrimination No. 3, 1 μM reverse primer described above, and 1.6 mM $MgCl_2$.

This reaction solution was subjected to a PCR reaction using LightCycler that is a thermal cycler manufactured by Roche Diagnostics, under the condition of denaturation step: 94° C., 10 sec; annealing step: 58° C., 10 sec; extension step: 72° C., 10 sec; and cycle number: 20 cycles.

Results of each PCR reaction were analyzed using Bioanalyzer 2100 that is a system for DNA electrophoresis manufactured by Agilent Technologies Inc.

The concentrations obtained from the analysis were further mathematically processed as described below.

The highest concentration of a target PCR product in each of Discrimination 1, Discrimination 2 and Discrimination 3 was obtained when a wild type λDNA was used as a template and λ1-CAA (Discrimination 1), λ2-GGC (Discrimination 2), or λ3-CTG (Discrimination 3) was used as a forward primer. The comparative concentration (%) of the target PCR product in each of Discrimination 1, Discrimination 2 and Discrimination 3 was calculated using the following equations 1, 2 and 3 with the above highest concentration of the target PCR products set to 100%.

Target PCR product comparative concentration (%) in Discrimination 1=100×(target PCR product concentration (nM))/(target PCR product concentration (nM) when a wild type λDNA is used as a template and λ1-CAA is used as a forward primer).    Equation 1

Target PCR product comparative concentration (%) in Discrimination 2=100×(target PCR product concentration (nM))/(target PCR product concentration (nM) when a wild type DNA is used as a template and λ2-GGC is used as a forward primer).    Equation 2

Target PCR product comparative concentration (%) in Discrimination 3=100×(target PCR product concentration (nM))/(target PCR product concentration (nM) when a wild type λDNA is used as a template and λ3-CTG is used as a forward primer).    Equation 3

Similarly, the comparative concentration (%) of a target PCR product in each of Example 1 and Comparative Example 1 was calculated using the following equation 4. That is, the highest concentration of a target PCR product in each of Example 1 and Comparative Example 1 was obtained when a wild type λDNA was used as a template and λ-GTT was used as a forward primer. The comparative concentration (%) of the target PCR product in each of Example 1 and Comparative Example 1 was calculated using the following equation 4 with the above highest concentrations of the target PCR products set to 100%.

Target PCR product comparative concentration (%) in Example 1 or Comparative Example 1=100× (target PCR product concentration (nM)) /(target PCR product concentration (nM) when a wild type λDNA was used as a template and λ-GTT was used as a forward primer).    Equation 4

Among the target PCR product comparative concentrations (%) obtained from the above equations 1 to 4, those obtained when a wild type λDNA was used as a template and the second and third bases from the 3' end base of each forward primer are identical to each other were averaged. Similarly, the target PCR product comparative concentrations (%) obtained when a mutation type λDNA was used as a template and the second and third bases from the 3' end base of each forward primer are identical to each other were averaged.

Therefore, the following 18 kinds of averages were obtained.

Averages 1

Averages of target PCR product comparative concentrations (%) of the following 4 kinds of combinations (of template/forward primer).

(Wild type λDNA/λ-TAT)

(Wild type λDNA/λ1-TAA)

(Wild type λDNA/λ2-TAC)

(Wild Type λDNA/λ3-Tag)

Averages 2

Averages of target PCR product comparative concentrations (%) of the following 4 kinds of combinations (of template/forward primer).

(Mutant type λDNA-6965-GC/λ-TAT)

(Mutant type λDNA-7248-GC/λ1-TAA)

(Mutant type λDNA-7064-AT/λ2-TAC)

(Mutant type λDNA-7011-AT/λ3-TAG)

Averages 3
Averages of target PCR product comparative concentrations (%) of the following 4 kinds of combinations (of template/forward primer).

(Wild type λDNA/λ-TTT)

(Wild type λDNA/λ1-TTA)

(Wild type λDNA/λ2-TTC)

(Wild Type λDNA/λ3-Ttg)

Averages 4
Averages of target PCR product comparative concentrations (%) of the following 4 kinds of combinations (of template/forward primer).

(Mutant type λDNA-6965-GC/λ-TTT)

(Mutant type λDNA-7248-GC/λ1-TTA)

(Mutant type λDNA-7064-AT/λ2-TTC)

(Mutant type λDNA-7011-AT/λ3-TTG)

Averages 5
Averages of target PCR product comparative concentrations (%) of the following 4 kinds of combinations (of template/forward primer).

(Wild type λDNA/λ-TGT)

(Wild type λDNA/λ1-TGA)

(Wild type λDNA/λ2-TGC)

(Wild Type λDNA/λ3-TGG)

Averages 6
Averages of target PCR product comparative concentrations (%) of the following 4 kinds of combinations (of template/forward primer).

(Mutant type λDNA-6965-GC/λ-TGT)

(Mutant type λDNA-7248-GC/λ1-TGA)

(Mutant type λDNA-7064-AT/λ2-TGC)

(Mutant type λDNA-7011-AT/λ3-TGG)

Averages 7
Averages of target PCR product comparative concentrations (%) of the following 4 kinds of combinations (of template/forward primer)

(Wild type λDNA/λ-GAT)

(Wild type λDNA/λ1-GAA)

(Wild type λDNA/λ2-GAC)

(Wild Type λDNA/λ3-GAG)

Averages 8
Averages of target PCR product comparative concentrations (%) of the following 4 kinds of combinations (of template/forward primer).

(Mutant type λDNA-6965-GC/λ-GAT)

(Mutant type λDNA-7248-GC/λ1-GAA)

(Mutant type λDNA-7064-AT/λ2-GAC)

(Mutant type λDNA-7011-AT/λ3-GAG)

Averages 9
Averages of target PCR product comparative concentrations (%) of the following 4 kinds of combinations (of template/forward primer)

(Wild type λNA/λ-GTT)

(Wild type λDNA/λ1-GTA)

(Wild type λDNA/λ2-GTC)

(Wild Type λDNA/λ3-GTG)

Averages 10
Averages of target PCR product comparative concentrations (%) of the following 4 kinds of combinations (of template/forward primer).

(Mutant type λDNA-6965-GC/λ-GTT)

(Mutant type λDNA-7248-GC/λ1-GTA)

(Mutant type λDNA-7064-AT/λ2-GTc)

(Mutant type λNA-7011-AT/λ3-GTG)

Averages 11
Averages of target PCR product comparative concentrations (%) of the following 4 kinds of combinations (of template/forward primer)

(Wild type λDNA/λ-GGT)

(Wild type λDNA/λ1-GGA)

(Wild type λDNA/λ2-GGC)

(Wild Type λDNA/λ3-GGG)

Averages 12
Averages of target PCR product comparative concentrations (%) of the following 4 kinds of combinations (of template/forward primer).

(Mutant type λDNA-6965-GC/λ-GGT)

(Mutant type λDNA-7248-GC/λ1-GGA)

(Mutant type λDNA-7064-AT/λ2-GGC)

(Mutant type λDNA-7011-AT/λ3-GGG)

Averages 13
Averages of target PCR product comparative concentrations (%) of the following 4 kinds of combinations (of template/forward primer).

(Wild type λDNA/λ-CAT)

(Wild type λDNA/λ1-CAA)

(Wild type λDNA/λ2-CAC)

(Wild Type λDNA/λ3-CAG)

Averages 14
Averages of target PCR product comparative concentrations (%) of the following 4 kinds of combinations (of template/forward primer).

(Mutant type λDNA-6965-GC/λ-CAT)

(Mutant type λDNA-7248-GC/λ1-CAA)

(Mutant type λDNA-7064-AT/λ2-CAC)

(Mutant type λDNA-7011-AT/λ3-CAG)

Averages 15
Averages of target PCR product comparative concentrations (%) of the following 4 kinds of combinations (of template/forward primer).

(Wild type λDNA/λ-CTT)

(Wild type λDNA/λ1-CTA)

(Wild type λDNA/λ2-CTC)

(Wild Type λDNA/λ3-CTG)

Averages 16

Averages of target PCR product comparative concentrations (%) of the following 4 kinds of combinations (of template/forward primer).

(Mutant type λDNA-6965-GC/λ-CTT)

(Mutant type λDNA-7248-GC/λ1-CTA)

(Mutant type λDNA-7064-AT/λ2-CTC)

(Mutant type λDNA-7011-AT/λ3-CTG)

Averages 17

Averages of target PCR product comparative concentrations (%) of the following 4 kinds of combinations (of template/forward primer).

(Wild type λDNA/λ-CGT)

(Wild type λDNA/λ1-CGA)

(Wild type λDNA/λ2-CGC)

(Wild Type λDNA/λ3-CGG)

Averages 18

Averages of target PCR product comparative concentrations (%) of the following 4 kinds of combinations (of template/forward primer).

(Mutant type λDNA-6965-GC/λ-CGT)

(Mutant type λDNA-7248-GC/λ1-CGA)

(Mutant type λDNA-7064-AT/λ2-CGC)

(Mutant type λDNA-7011-AT/λ3-CGG)

Figure 7:
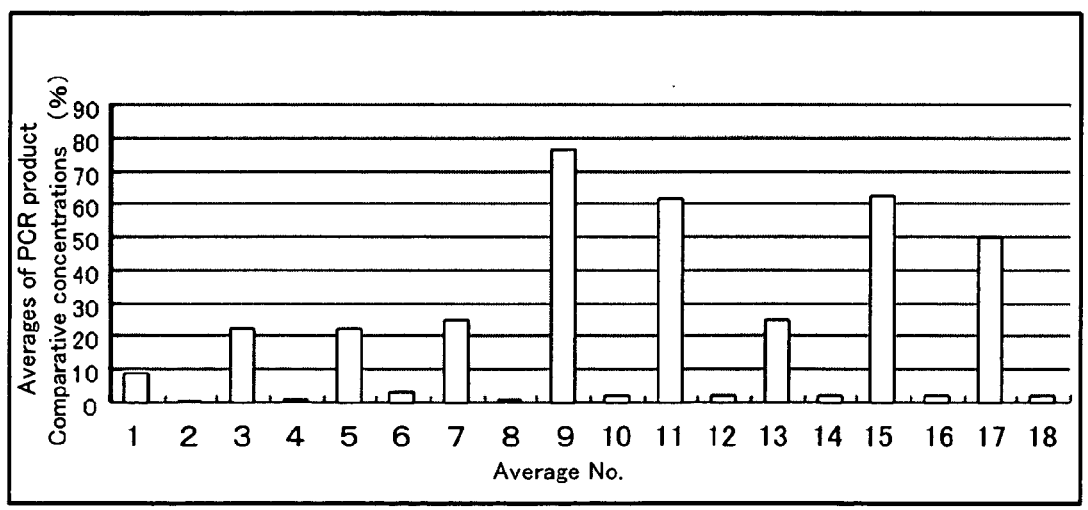
FIG. 7 is a graph presenting experimental results in Example 2.

Averages 1 to 18 are illustrated in FIG. 7.

As can be seen from the drawing, the average values obtained when a mutation type λDNA was used as a template (average values 2, 4, 6, 8, 10, 12, 14, 16, 18) are generally small. In other words, PCR reactions for discrimination were suppressed irrespective of the second and third bases from 3' terminal base of each forward primer.

On the other hand, the average values obtained when a mutation type λDNA was used as a template (average values 1, 3, 5, 7, 9, 11, 13, 15, 17) are significantly greater than the corresponding average values obtained when a mutation type λDNA was used as a template and the second and third bases from the 3' end base of each forward primer are identical to each other (pairs of average values: 1 and 2, 3 and 4, 5 and 6, 7 and 8, 9 and 10, 11 and 12, 13 and 14, 15 and 16, and 17 and 18). More specifically, the differences between the average values obtained when a wild type λDNA was used as a template and the average values obtained when a mutation type λNA was used as a template are apparently greater when the second and third bases from the 3' end base of each forward primer are 5'-GT-3', 5'-GG-3', 5'-CT-3' or 5'-CG-3' than when the second and third bases from the 3' end base of each forward primer are others.

As is seen from these result, extremely high discrimination capability can be attained when a base immediately adjacent to on the 3' end side of the target SNP base is G; a base adjacent with one base spaced apart is T; the second base from the 3' end of the allele specific primer is T or G; and the third base is G or C.

According to the present invention, a method of discriminating a target base carried by a DNA which is accompanied by less possibility of the false positive and enables definite discrimination of SNP or the like is provided.

From the foregoing descriptions, many modifications and other embodiments of the present invention will be apparent to persons skilled in the art. Therefore, the foregoing descriptions should be construed as just for illustrative exemplification, provided for the purpose of teaching the best embodiment for carrying out the present invention to persons skilled in the art. Details of construction and/or function of the present invention can be substantially altered without departing from the spirit thereof.

What is claimed is:

1. A method for discriminating a target base carried by a target DNA, comprising:
   (1) a DNA elongation step comprising
      (a) binding to said target DNA a test allele specific primer,
      wherein said target DNA comprises the sequence 3'-(T-G-S1)-5', S1 being the target base, and
      wherein said test allele specific primer comprises the sequence 5'-(B3-B2-S1')-3', (B3, B2) being bases selected from the group consisting of (G, T), (G, G), (C, T), and (C, G),
      wherein S1' is the 3' terminal base of the test allele specific primer and is complimentary to the base predicted to be S1; and
      (b) causing a test DNA elongation reaction; and
   (2) a discrimination step comprising measuring the efficiency of said DNA elongation to discriminate that said target is the same as said predicted base, or that said target base is distinct from said predicted base.

2. The method according to claim 1 wherein said DNA elongation reaction is a primer extension reaction.

3. The method according to claim 1 wherein said DNA elongation reaction is a primer extension reaction relied solely on said allele specific primer.

4. The method according to claim 2 wherein said efficiency is measured by determining the concentration of pyrophosphate produced by said primer extension reaction.

5. The method according to claim 4 wherein said concentration of pyrophosphate is detected in terms of luminescence intensity.

6. The method according to claim 1 wherein said DNA elongation reaction is a PCR reaction.

7. The method according to claim 6 wherein said efficiency is examined by measuring the concentration of the amplified DNA produced by said PCR reaction with an electrophoretic method.

* * * * *

SEQUENCE LISTING

```
<160> NUMBER OF SEQ ID NOS: 46

<210> SEQ ID NO 1
<211> LENGTH: 25
<212> TYPE: DNA
<213> ORGANISM: Enterobacteria lambda phage

<400> SEQUENCE: 1
caacacgatg gtgctgggga acgtt                                  25

<210> SEQ ID NO 2
<211> LENGTH: 25
<212> TYPE: DNA
<213> ORGANISM: Enterobacteria lambda phage

<400> SEQUENCE: 2
caacacgatg gtgctgggga acggt                                  25

<210> SEQ ID NO 3
<211> LENGTH: 25
<212> TYPE: DNA
<213> ORGANISM: Enterobacteria lambda phage
```

```
<400> SEQUENCE: 3
caacacgatg gtgctgggga acctt                                              25

<210> SEQ ID NO 4
<211> LENGTH: 25
<212> TYPE: DNA
<213> ORGANISM: Enterobacteria lambda phage

<400> SEQUENCE: 4
caacacgatg gtgctgggga accgt                                              25

<210> SEQ ID NO 5
<211> LENGTH: 25
<212> TYPE: DNA
<213> ORGANISM: Enterobacteria lambda phage

<400> SEQUENCE: 5
agtgttcccc agcaccatcg tgttg                                              25

<210> SEQ ID NO 6
<211> LENGTH: 25
<212> TYPE: DNA
<213> ORGANISM: Mutant Enterobacteria lambda phage
<220> FEATURE:
<221> NAME/KEY: mutation
<222> LOCATION: (1)..(1)

<400> SEQUENCE: 6
cgtgttcccc agcaccatcg tgttg                                              25

<210> SEQ ID NO 7
<211> LENGTH: 25
<212> TYPE: DNA
<213> ORGANISM: Enterobacteria lambda phage

<400> SEQUENCE: 7
gaatcacggt atccggctgc gctga                                              25

<210> SEQ ID NO 8
<211> LENGTH: 25
<212> TYPE: DNA
<213> ORGANISM: Enterobacteria lambda phage
<220> FEATURE:
<221> NAME/KEY: mutation
<222> LOCATION: (1)..(1)

<400> SEQUENCE: 8
tcagcgcagc cggataccgt gattc                                              25

<210> SEQ ID NO 9
<211> LENGTH: 25
<212> TYPE: DNA
<213> ORGANISM: Enterobacteria lambda phage

<400> SEQUENCE: 9
caacacgatg gtgctgggga actat                                              25

<210> SEQ ID NO 10
<211> LENGTH: 25
<212> TYPE: DNA
<213> ORGANISM: Enterobacteria lambda phage

<400> SEQUENCE: 10
caacacgatg gtgctgggga acttt                                              25
```

-continued

```
<210> SEQ ID NO 11
<211> LENGTH: 25
<212> TYPE: DNA
<213> ORGANISM: Enterobacteria lambda phage

<400> SEQUENCE: 11
caacacgatg gtgctgggga actgt                                              25

<210> SEQ ID NO 12
<211> LENGTH: 25
<212> TYPE: DNA
<213> ORGANISM: Enterobacteria lambda phage

<400> SEQUENCE: 12
caacacgatg gtgctgggga acgat                                              25

<210> SEQ ID NO 13
<211> LENGTH: 25
<212> TYPE: DNA
<213> ORGANISM: Enterobacteria lambda phage

<400> SEQUENCE: 13
caacacgatg gtgctgggga accat                                              25

<210> SEQ ID NO 14
<211> LENGTH: 22
<212> TYPE: DNA
<213> ORGANISM: Enterobacteria lambda phage

<400> SEQUENCE: 14
gtctccgctc gctgggtgat aa                                                 22

<210> SEQ ID NO 15
<211> LENGTH: 22
<212> TYPE: DNA
<213> ORGANISM: Enterobacteria lambda phage

<400> SEQUENCE: 15
gtctccgctc gctgggtgat ta                                                 22

<210> SEQ ID NO 16
<211> LENGTH: 22
<212> TYPE: DNA
<213> ORGANISM: Enterobacteria lambda phage

<400> SEQUENCE: 16
gtctccgctc gctgggtgat ga                                                 22

<210> SEQ ID NO 17
<211> LENGTH: 22
<212> TYPE: DNA
<213> ORGANISM: Enterobacteria lambda phage

<400> SEQUENCE: 17
gtctccgctc gctgggtgag aa                                                 22

<210> SEQ ID NO 18
<211> LENGTH: 22
<212> TYPE: DNA
<213> ORGANISM: Enterobacteria lambda phage

<400> SEQUENCE: 18
```

```
gtctccgctc gctgggtgag ta                                              22
```

<210> SEQ ID NO 19
<211> LENGTH: 22
<212> TYPE: DNA
<213> ORGANISM: Enterobacteria lambda phage

<400> SEQUENCE: 19

```
gtctccgctc gctgggtgag ga                                              22
```

<210> SEQ ID NO 20
<211> LENGTH: 22
<212> TYPE: DNA
<213> ORGANISM: Enterobacteria lambda phage

<400> SEQUENCE: 20

```
gtctccgctc gctgggtgac aa                                              22
```

<210> SEQ ID NO 21
<211> LENGTH: 22
<212> TYPE: DNA
<213> ORGANISM: Enterobacteria lambda phage

<400> SEQUENCE: 21

```
gtctccgctc gctgggtgac ta                                              22
```

<210> SEQ ID NO 22
<211> LENGTH: 22
<212> TYPE: DNA
<213> ORGANISM: Enterobacteria lambda phage

<400> SEQUENCE: 22

```
gtctccgctc gctgggtgac ga                                              22
```

<210> SEQ ID NO 23
<211> LENGTH: 22
<212> TYPE: DNA
<213> ORGANISM: Enterobacteria lambda phage

<400> SEQUENCE: 23

```
tgttcaccca gcgagcggag ac                                              22
```

<210> SEQ ID NO 24
<211> LENGTH: 22
<212> TYPE: DNA
<213> ORGANISM: Mutant Enterobacteria lambda phage
<220> FEATURE:
<221> NAME/KEY: mutation
<222> LOCATION: (1)..(1)

<400> SEQUENCE: 24

```
cgttcaccca gcgagcggag ac                                              22
```

<210> SEQ ID NO 25
<211> LENGTH: 25
<212> TYPE: DNA
<213> ORGANISM: Enterobacteria lambda phage

<400> SEQUENCE: 25

```
ccgttacccg aaaaactggg tgtac                                           25
```

<210> SEQ ID NO 26
<211> LENGTH: 25
<212> TYPE: DNA

```
<213> ORGANISM: Enterobacteria lambda phage

<400> SEQUENCE: 26
ccgttacccg aaaaactggg tgttc                                    25

<210> SEQ ID NO 27
<211> LENGTH: 25
<212> TYPE: DNA
<213> ORGANISM: Enterobacteria lambda phage

<400> SEQUENCE: 27
ccgttacccg aaaaactggg tgtgc                                    25

<210> SEQ ID NO 28
<211> LENGTH: 25
<212> TYPE: DNA
<213> ORGANISM: Enterobacteria lambda phage

<400> SEQUENCE: 28
ccgttacccg aaaaactggg tggac                                    25

<210> SEQ ID NO 29
<211> LENGTH: 25
<212> TYPE: DNA
<213> ORGANISM: Enterobacteria lambda phage

<400> SEQUENCE: 29
ccgttacccg aaaaactggg tggtc                                    25

<210> SEQ ID NO 30
<211> LENGTH: 25
<212> TYPE: DNA
<213> ORGANISM: Enterobacteria lambda phage

<400> SEQUENCE: 30
ccgttacccg aaaaactggg tgggc                                    25

<210> SEQ ID NO 31
<211> LENGTH: 25
<212> TYPE: DNA
<213> ORGANISM: Enterobacteria lambda phage

<400> SEQUENCE: 31
ccgttacccg aaaaactggg tgcac                                    25

<210> SEQ ID NO 32
<211> LENGTH: 25
<212> TYPE: DNA
<213> ORGANISM: Enterobacteria lambda phage

<400> SEQUENCE: 32
ccgttacccg aaaaactggg tgctc                                    25

<210> SEQ ID NO 33
<211> LENGTH: 25
<212> TYPE: DNA
<213> ORGANISM: Enterobacteria lambda phage

<400> SEQUENCE: 33
ccgttacccg aaaaactggg tgcgc                                    25

<210> SEQ ID NO 34
<211> LENGTH: 25
```

```
<212> TYPE: DNA
<213> ORGANISM: Enterobacteria lambda phage

<400> SEQUENCE: 34
ggtcacccag tttttcgggt aacgg                                              25

<210> SEQ ID NO 35
<211> LENGTH: 25
<212> TYPE: DNA
<213> ORGANISM: Mutant Enterobacteria lambda phage
<220> FEATURE:
<221> NAME/KEY: mutation
<222> LOCATION: (1)..(1)

<400> SEQUENCE: 35
tgtcacccag tttttcgggt aacgg                                              25

<210> SEQ ID NO 36
<211> LENGTH: 21
<212> TYPE: DNA
<213> ORGANISM: Enterobacteria lambda phage

<400> SEQUENCE: 36
gctgcattca ggatgcggta g                                                  21

<210> SEQ ID NO 37
<211> LENGTH: 21
<212> TYPE: DNA
<213> ORGANISM: Enterobacteria lambda phage

<400> SEQUENCE: 37
gctgcattca ggatgcggtt g                                                  21

<210> SEQ ID NO 38
<211> LENGTH: 21
<212> TYPE: DNA
<213> ORGANISM: Enterobacteria lambda phage

<400> SEQUENCE: 38
gctgcattca ggatgcggtg g                                                  21

<210> SEQ ID NO 39
<211> LENGTH: 21
<212> TYPE: DNA
<213> ORGANISM: Enterobacteria lambda phage

<400> SEQUENCE: 39
gctgcattca ggatgcggga g                                                  21

<210> SEQ ID NO 40
<211> LENGTH: 21
<212> TYPE: DNA
<213> ORGANISM: Enterobacteria lambda phage

<400> SEQUENCE: 40
gctgcattca ggatgcgggt g                                                  21

<210> SEQ ID NO 41
<211> LENGTH: 21
<212> TYPE: DNA
<213> ORGANISM: Enterobacteria lambda phage

<400> SEQUENCE: 41
gctgcattca ggatgcgggg g                                                  21
```

<210> SEQ ID NO 42
<211> LENGTH: 21
<212> TYPE: DNA
<213> ORGANISM: Enterobacteria lambda phage

<400> SEQUENCE: 42
gctgcattca ggatgcggca g                                              21

<210> SEQ ID NO 43
<211> LENGTH: 21
<212> TYPE: DNA
<213> ORGANISM: Enterobacteria lambda phage

<400> SEQUENCE: 43
gctgcattca ggatgcggct g                                              21

<210> SEQ ID NO 44
<211> LENGTH: 21
<212> TYPE: DNA
<213> ORGANISM: Enterobacteria lambda phage

<400> SEQUENCE: 44
gctgcattca ggatgcggcg g                                              21

<210> SEQ ID NO 45
<211> LENGTH: 21
<212> TYPE: DNA
<213> ORGANISM: Enterobacteria lambda phage

<400> SEQUENCE: 45
cgtccgcatc ctgaatgcag c                                              21

<210> SEQ ID NO 46
<211> LENGTH: 21
<212> TYPE: DNA
<213> ORGANISM: Mutant Enterobacteria lambda phage
<220> FEATURE:
<221> NAME/KEY: mutation
<222> LOCATION: (1)..(1)

<400> SEQUENCE: 46
tgtccgcatc ctgaatgcag c                                              21